United States Patent
Samandi et al.

(10) Patent No.: US 10,159,808 B2
(45) Date of Patent: *Dec. 25, 2018

(54) RETRACTABLE NEEDLE SAFETY SYRINGES

(71) Applicant: UNL Holdings LLC, New York, NY (US)

(72) Inventors: Masoud Samandi, Sparta, NJ (US); Christian P. Brandt, York, PA (US); Paul D. Goebel, Elizabethtown, PA (US)

(73) Assignee: UNL Holdings LLC, New York, NY (US)

( * ) Notice: Subject to any disclaimer, the term of this patent is extended or adjusted under 35 U.S.C. 154(b) by 766 days.

This patent is subject to a terminal disclaimer.

(21) Appl. No.: 14/242,076

(22) Filed: Apr. 1, 2014

(65) Prior Publication Data

US 2014/0213972 A1    Jul. 31, 2014

Related U.S. Application Data

(63) Continuation of application No. 13/693,915, filed on Dec. 4, 2012, now Pat. No. 8,702,653.

(Continued)

(51) Int. Cl.
| | | |
|---|---|---|
| *A61M 5/32* | (2006.01) | |
| *A61M 5/50* | (2006.01) | |
| *A61M 5/34* | (2006.01) | |

(52) U.S. Cl.
CPC ............. *A61M 5/50* (2013.01); *A61M 5/321* (2013.01); *A61M 5/3234* (2013.01); *A61M 5/34* (2013.01);

(Continued)

(58) Field of Classification Search
CPC ............ A61M 5/50; A61M 2005/5006; A61M 2207/00; A61M 5/3134; A61M 5/322;

(Continued)

(56) References Cited

U.S. PATENT DOCUMENTS

| | | |
|---|---|---|
| 4,838,863 A | 6/1989 | Allard et al. |
| 4,838,869 A | 6/1989 | Allard et al. |

(Continued)

FOREIGN PATENT DOCUMENTS

| | | |
|---|---|---|
| DE | 19740259 A | 3/1998 |
| EP | 1 300 173 B1 | 6/2006 |

(Continued)

OTHER PUBLICATIONS

European Patent Office, International Search Report in International Application No. PCT/US2012/067793, 5 pages (dated May 31, 2013).

(Continued)

*Primary Examiner* — Matthew F Desanto

(74) *Attorney, Agent, or Firm* — Hamilton, Brook, Smith & Reynolds, P.C.

(57) ABSTRACT

A barrel adapter mountable to a syringe barrel includes a barrel tip, a biasing member, a locking mechanism, and a needle assembly. A safety syringe includes a barrel, a plunger assembly, and a barrel adapter. The needle assembly includes a needle, a needle hub, and a needle seal. The needle is configured to pass-through the needle assembly, locking mechanism, biasing member, and barrel tip such that, at one end the needle is within the barrel and at another end the needle passes through an aperture in the barrel tip. The barrel may be substantially cylindrical, having along its longitudinal axis a distal end for drug injection, a proximal end for injection control, and at least a portion of the barrel interior for drug containment. The barrel adapter provides (Continued)

needle retraction mechanisms to the barrel to form a safety syringe. Methods of assembling, manufacturing, and using such syringes are also provided.

20 Claims, 6 Drawing Sheets

Related U.S. Application Data

(60) Provisional application No. 61/602,277, filed on Feb. 23, 2012, provisional application No. 61/639,898, filed on Apr. 28, 2012, provisional application No. 61/667,010, filed on Jul. 2, 2012.

(52) U.S. Cl.
CPC ............... *A61M 2005/3226* (2013.01); *A61M 2005/3236* (2013.01); *A61M 2207/00* (2013.01); *Y10T 29/49826* (2015.01)

(58) Field of Classification Search
CPC ........ A61M 2005/3228; A61M 5/3234; A61M 2005/3235; A61M 2005/3238
USPC ........................................................ 604/110
See application file for complete search history.

(56) References Cited

U.S. PATENT DOCUMENTS

| | | | |
|---|---|---|---|
| 4,874,382 A | 10/1989 | Lindemann et al. | |
| 4,927,414 A | 5/1990 | Kulli | |
| 4,994,034 A | 2/1991 | Botich et al. | |
| 5,053,010 A | 10/1991 | McGary et al. | |
| 5,114,410 A | 5/1992 | Caralt Batlle | |
| 5,180,369 A | 1/1993 | Dysarz | |
| 5,180,370 A | 1/1993 | Gillespie | |
| 5,188,599 A | 2/1993 | Botich et al. | |
| 5,211,629 A | 5/1993 | Pressly et al. | |
| 5,304,138 A | 4/1994 | Mercado | |
| 5,342,310 A | 8/1994 | Ueyama et al. | |
| 5,346,480 A | 9/1994 | Hess et al. | |
| 5,385,551 A | 1/1995 | Shaw | |
| 5,389,076 A | 2/1995 | Shaw | |
| 5,466,233 A | 11/1995 | Weiner et al. | |
| 5,578,011 A | 11/1996 | Shaw | |
| 5,613,952 A | 3/1997 | Pressly, Sr. et al. | |
| 5,769,822 A | 6/1998 | McGary et al. | |
| 5,800,403 A | 9/1998 | Pressly, Sr. et al. | |
| 5,941,250 A | 8/1999 | Aramant et al. | |
| 6,015,438 A | 1/2000 | Shaw | |
| 6,074,370 A | 6/2000 | Pressly, Sr. et al. | |
| 6,123,683 A | 9/2000 | Propp | |
| 6,159,218 A | 12/2000 | Aramant et al. | |
| 6,190,350 B1 | 2/2001 | Davis et al. | |
| 6,447,522 B2 | 9/2002 | Gambale et al. | |
| 6,450,937 B1 | 9/2002 | Mercerau et al. | |
| 6,478,768 B1 | 11/2002 | Kneer | |
| 6,478,776 B1 | 11/2002 | Rosenman et al. | |
| 6,494,863 B1 | 12/2002 | Shaw et al. | |
| 6,558,357 B1 | 5/2003 | Hoeck | |
| 6,605,073 B1 | 8/2003 | Pressly, Sr. et al. | |
| 6,632,171 B2 | 10/2003 | Iddan et al. | |
| 6,673,044 B2 | 1/2004 | Righi et al. | |
| 6,752,782 B2 | 6/2004 | Liao | |
| 6,899,717 B2 | 5/2005 | Weber et al. | |
| 7,014,622 B1* | 3/2006 | Pressly, Sr. ......... | A61M 5/3234 604/110 |
| 7,090,681 B2 | 8/2006 | Weber et al. | |
| 7,147,644 B2 | 12/2006 | Weber et al. | |
| 7,329,238 B2 | 2/2008 | Halseth et al. | |
| 7,468,065 B2 | 12/2008 | Weber et al. | |
| 7,572,247 B2 | 8/2009 | Smith et al. | |
| 7,604,613 B2 | 10/2009 | Crawford et al. | |
| 7,713,244 B1 | 5/2010 | Cherif Cheikh et al. | |
| 7,753,916 B2 | 7/2010 | Weber et al. | |
| 7,806,858 B2 | 10/2010 | Smith et al. | |
| 7,947,020 B2 | 5/2011 | Thayer | |
| 7,972,300 B2 | 7/2011 | Smith et al. | |
| 7,972,301 B2 | 7/2011 | Oliver | |
| 7,976,489 B2 | 7/2011 | Lawter et al. | |
| 7,988,663 B2 | 8/2011 | Schiller et al. | |
| 7,993,307 B2 | 8/2011 | Lin | |
| 7,998,108 B2 | 8/2011 | Nazzaro et al. | |
| 8,029,458 B2 | 10/2011 | Cherif-Cheikh et al. | |
| 8,088,104 B2 | 1/2012 | Smith et al. | |
| 8,152,762 B2 | 4/2012 | Smith et al. | |
| 8,192,408 B2 | 6/2012 | Nazzaro et al. | |
| 8,242,099 B2 | 8/2012 | Wong et al. | |
| 8,343,094 B2 | 1/2013 | Shaw | |
| 8,702,653 B2* | 4/2014 | Samandi ............... | A61M 5/321 604/110 |
| 8,979,795 B2 | 3/2015 | Bokelman et al. | |
| 9,050,415 B2 | 6/2015 | Shetty et al. | |
| 2003/0233101 A1 | 12/2003 | Lubock et al. | |
| 2006/0084943 A1 | 4/2006 | Rosenman et al. | |
| 2007/0178138 A1 | 8/2007 | Pal et al. | |
| 2008/0097337 A1 | 4/2008 | Judd | |
| 2009/0118703 A1 | 5/2009 | Orilla et al. | |
| 2009/0209903 A1 | 8/2009 | Cherif-Cheikh et al. | |
| 2009/0258924 A1 | 10/2009 | Lyons et al. | |
| 2011/0040245 A1 | 2/2011 | Garcia De Castro Andrews | |
| 2011/0152755 A1 | 6/2011 | Scmalz | |
| 2011/0190699 A1 | 8/2011 | Judd et al. | |
| 2011/0230844 A1 | 9/2011 | Shaw et al. | |
| 2011/0275891 A1 | 11/2011 | Shemi | |
| 2012/0123324 A1 | 5/2012 | Schmalz | |
| 2013/0226084 A1 | 8/2013 | Samandi et al. | |
| 2013/0237910 A1 | 9/2013 | Shetty et al. | |
| 2014/0276446 A1 | 9/2014 | Bokelman et al. | |
| 2015/0202419 A1 | 7/2015 | Wetzel et al. | |
| 2015/0238745 A1 | 8/2015 | Shetty et al. | |

FOREIGN PATENT DOCUMENTS

| | | |
|---|---|---|
| EP | 2011530 A1 | 1/2009 |
| EP | 1 633 433 B1 | 4/2010 |
| EP | 2229969 A | 9/2010 |
| JP | 2011-125724 A | 6/2011 |
| RU | 2010132226 A | 2/2012 |
| WO | WO 2005-072802 A1 | 8/2005 |
| WO | WO 2006-024172 A | 3/2006 |
| WO | WO 2012/027182 A2 | 3/2012 |
| WO | 2013126853 A2 | 8/2013 |
| WO | 2016160004 A1 | 10/2016 |

OTHER PUBLICATIONS

European Patent Office, Written Opinion of the International Searching Authority in International Application No. PCT/US2012/067793, 5 pages (dated May 31, 2013).

European Patent Office, International Search Report in International Patent Application No. PCT/US2013/027529, 5 pages (dated Sep. 2, 2013).

European Patent Office, Written Opinion of the International Searching Authority in International Patent Application No. PCT/US2013/027529, 6 pages (dated Sep. 2, 2013).

Notification of Transmittal of the International Search Report and the Written Opinion of the International Searching Authority, or the Declaration, for International Application No. PCT/US2015/023789, entitled: "Devices for Targeted Delivery of Therapeutic Implants," dated Feb. 3, 2016 (11 pgs).

International Preliminary Report on Patentability for International Application No. PCT/US2015/023789, entitled: "Devices for Targeted Delivery of Therapeutic Implants," dated Oct. 3, 2017 (6 pgs).

International Preliminary Report on Patentability for International Application No. PCT/US2012/067793, entitled: "Retractable Needle Safety Syringes," dated Jul. 29, 2014 (14 pgs).

International Preliminary Report on Patentability for International Application No. PCT/US2013/027529, entitled: "Devices for Tar-

(56) References Cited

OTHER PUBLICATIONS geted Delivery of Therapeutic Implants," dated Aug. 26, 2014 (7 pgs).

* cited by examiner

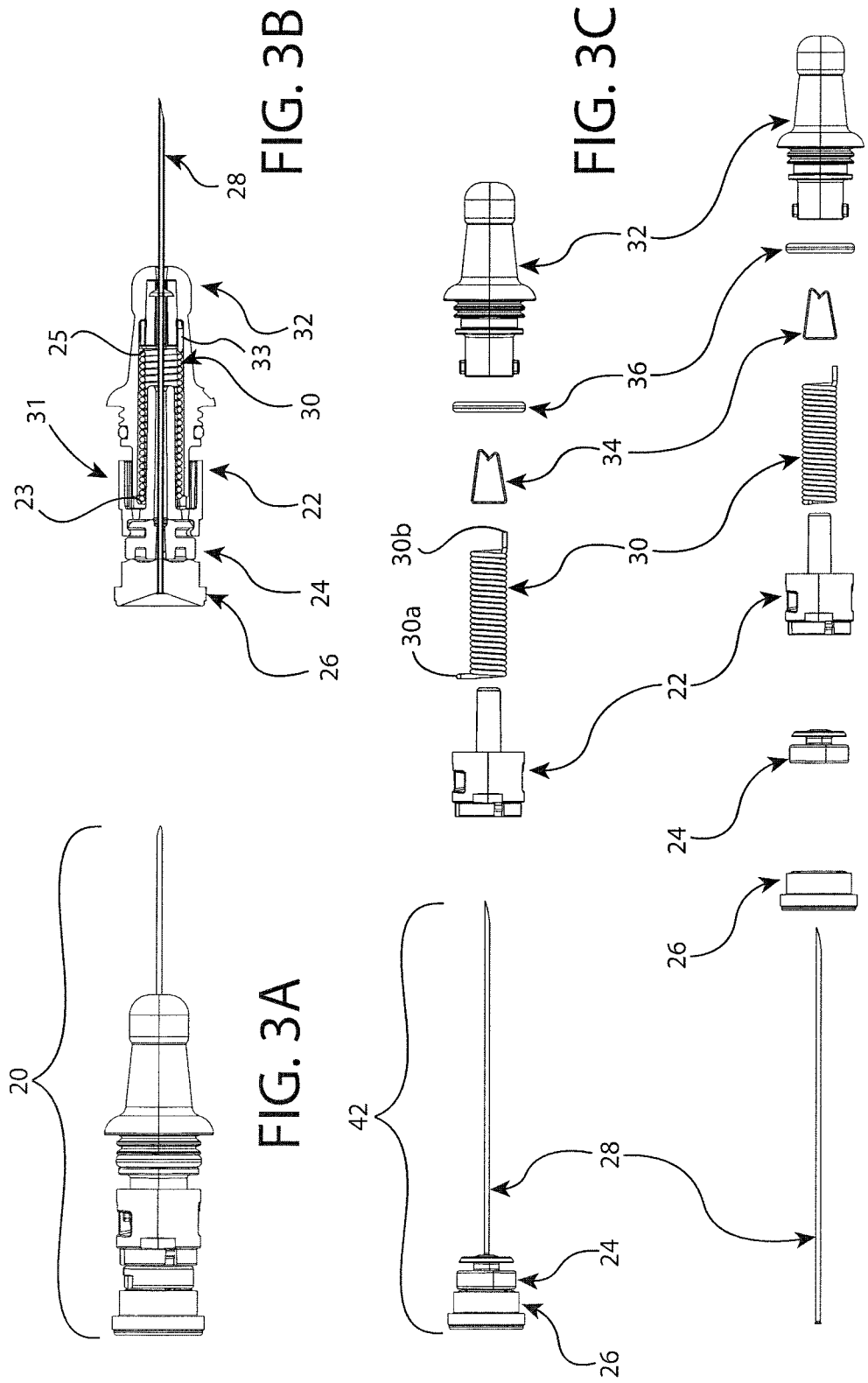

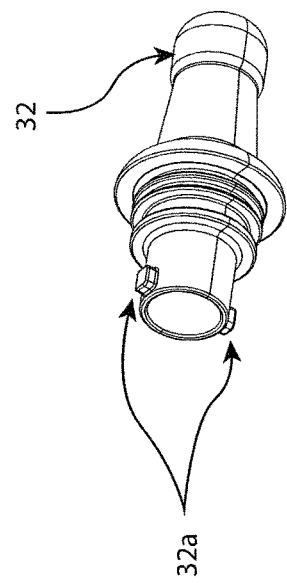
FIG. 5
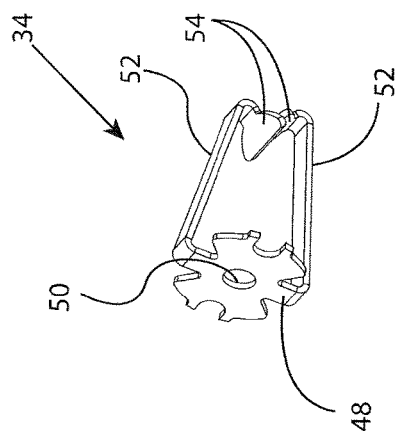
FIG. 7
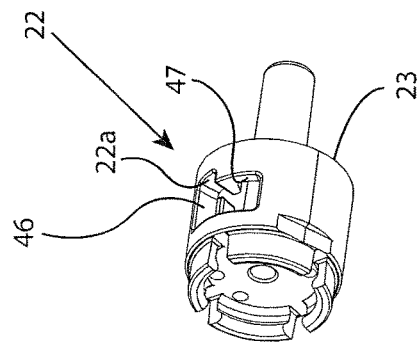
FIG. 4
FIG. 6

RETRACTABLE NEEDLE SAFETY SYRINGES

CROSS-REFERENCE TO RELATED APPLICATIONS

This application is a continuation of U.S. application Ser. No. 13/693,915 filed Dec. 4, 2012, which claims priority to U.S. Provisional Application No. 61/602,277, filed on Feb. 23, 2012; U.S. Provisional Application No. 61/639,898, filed on Apr. 28, 2012; and U.S. Provisional Application No. 61/667,010, filed on Jul. 2, 2012, each of which is included by reference herein in their entirety for all purposes.

FIELD OF THE INVENTION

The present invention relates to safety syringes. More specifically, the embodiments of the present invention relate to barrel-adaptable needle retraction systems, syringes which integrate such safety mechanisms, methods for manufacturing such safety syringes, and their methods of use.

BACKGROUND OF THE INVENTION

Manually activated pre-filled syringe cartridges are commercially available from a variety of manufacturers, including the owner and assignee of the present invention. Pre-filled syringe cartridges are used in the administration of drug solutions, drug suspensions, vaccines, medicinal therapies, and any other liquid medicament by parenteral injection.

As such, pre-filled syringe cartridges include a primary drug chamber, a hypodermic needle permanently affixed to and in fluid communication with the drug chamber, and a piston slidably received in the drug chamber. The pistons of the pre-filled syringe cartridges often include a plunger sub-assembly, which may include a plunger inner and a plunger outer, to force the liquid medicament from the needle. Pre-filled syringes are typically prepared by pharmaceutical companies or sterile filling contractors in a sterile filling room in which the drug and the syringe are brought together in a sterile manufacturing environment wherein all components and drug solutions are isolated from microbial contamination.

The practice of sharing syringes without adequate sterilization between successive users is a major contributor to the transfer of Human Immunodeficiency Virus (HIV) and Hepatitis with subsequent severe repercussions for the sufferer and at a high cost to society for supporting and providing medical attention to sufferers.

Furthermore, health professionals may be exposed to used syringes, which can lead to inadvertent needlestick injuries and possible exposure to infective pathogens or other contaminants. In response to this problem, retractable syringes have been developed with the aim of preventing syringe re-use and/or needlestick injury by used syringes.

In developing such retractable syringes, relatively complicated retractable needle assemblies have been devised which often are developed for a particular syringe barrel shape or configuration and cannot be readily mounted to a syringe barrel having a different shape or configuration. This is particularly a problem with glass syringe barrels, which are generally in short supply, many of which glass barrels do not have a desired shape or configuration for mounting a retractable needle assembly. Accordingly, many existing safety syringes require specifically-tailored retraction mechanisms and barrel configurations, which may require complex manufacturing processes or operational changes. The materials employed in the manufacture of such safety syringes must meet complex criteria for regulatory approval. Additionally, safety syringes must remain aesthetically-similar to conventional syringes to facilitate broad adoption and must be easy-to-use for self-administering patients.

BRIEF SUMMARY OF THE INVENTION

Embodiments of the present invention relate to barrel-adaptable needle retraction systems, syringes which integrate such safety mechanisms, methods of manufacturing such safety syringes, and their methods of use. Embodiments of the present invention provide reliable needle retraction, for improved user safety, without requiring complex manufacturing processes or operational changes for pharmaceutical companies or contract drug fillers. Additionally, embodiments of the present invention provide configurations which utilize materials and components which are readily employable for pharmaceutical use, many of which are increasingly considered off-the-shelf or standard components. Furthermore, the present invention provides components and devices which are aesthetically-similar to conventional syringes, which do not have needle retraction mechanisms, are ergonomically attractive to end-users, such as a medical practitioners and self-administering patients, and provide highly desired integrated safety features. The novel barrel adapters of the present invention are notably able to be adapted to primary drug barrels of varying configurations and materials such as, preferably, straight-barrel glass barrels to provide integrated needle assemblies and retraction mechanisms to the barrel. Such embodiments may be utilized for pre-filled or fill at time-of-use injectable drug syringes. As such, the adaptable retraction mechanisms of the present invention may be flexibly attached, affixed, mounted, or otherwise mated to standard barrels, such as straight-glass barrels. These embodiments, accordingly, provide novel and cost-efficient components and devices which are readily integrated into drug filling processes.

In an aspect of embodiments of the invention, there is provided a barrel adapter for a safety syringe having a barrel and a plunger assembly adapted to move within the barrel. The barrel adapter includes a barrel tip adapted to be sealingly engaged with a distal end of the barrel, a needle assembly, and a needle retraction mechanism. The needle assembly includes a needle, a needle hub through which the needle extends, and a needle seal. The needle assembly is disposed at least partially within the barrel tip, and adapted to move from an injection position in which the needle extends from a distal end of the barrel tip to a retracted position in which the needle is disposed within at least one of the barrel tip or the barrel. The needle retraction mechanism includes a biasing member and an actuable locking arrangement. The locking arrangement is disposed to maintain the biasing member in an energized position when the locking arrangement is locked and release the biasing member when actuated. The locking arrangement is actuable by depression of the plunger assembly, the biasing member being disposed to move the needle from the injection position to the retracted position when the biasing member is released from the energized position.

In a further aspect of embodiments of the invention, there is provided an automatically retractable safety syringe including a barrel having a distal end and a proximal end, a plunger assembly adapted to move within the barrel, and a barrel adapter sealingly engaged with the distal end of the barrel. The barrel adapter includes a barrel tip adapted to be sealingly engaged with a distal end of the barrel, a needle assembly, and a needle retraction mechanism. The needle assembly includes a needle, a needle hub through which the needle extends, and a needle seal. The needle assembly is disposed at least partially within the barrel tip, and adapted to move from an injection position in which the needle extends from a distal end of the barrel tip to a retracted position in which the needle is disposed within at least one of the barrel tip or the barrel. The needle retraction mechanism includes a biasing member and an actuable locking arrangement. The locking arrangement is disposed to maintain the biasing member in an energized position when the locking arrangement is locked and release the biasing member when actuated. The locking arrangement is actuable by depression of the plunger assembly, the biasing member being disposed to move the needle from the injection position to the retracted position when the biasing member is released from the energized position.

In another aspect of embodiments of the invention, there is provided a method of assembling an automatically retractable safety syringe. The method includes the steps of disposing a plunger assembly to move within a barrel, sealingly engaging a barrel tip with a distal end of the barrel, disposing a needle assembly for movement within the barrel tip and the barrel between an injection position wherein a needle of the needle assembly extends from the barrel tip and a retracted position wherein the needle is disposed within at least one of the barrel tip or the barrel, and disposing a needle retraction mechanism including a biasing member and an actuable locking arrangement within the barrel. The locking arrangement is disposed to maintain the biasing member in an energized position when the locking arrangement is locked and release the biasing member when actuated. The locking arrangement is actuable by depression of the plunger assembly, the biasing member being disposed to move the needle from the injection position to the retracted position when the biasing member is released from the energized position.

In a first particular embodiment, the present invention provides a barrel adapter that facilitates mounting of a needle assembly to a syringe barrel and includes a needle retraction mechanism. The barrel adapter includes a barrel tip, a biasing member, a locking mechanism, and a needle assembly. The needle assembly may generally include a needle, a needle hub, and a needle seal. The needle is configured to pass-through the needle assembly, locking mechanism, biasing member, and barrel tip such that, at one end, the needle is within the barrel and, at another end, the needle passes through an aperture in the barrel tip. In some embodiments, the needle hub and needle seal may be one component, while in other embodiments they may comprise two or more components. For example, in one embodiment the needle hub and needle seal are a unified unit such as a dual-shot plastic needle hub and elastomeric needle seal. Aspects of the needle assembly, such as the needle hub and/or the needle seal, may be utilized to retain the needle. The retention of the needle may be achieved by mechanical retention, molded retention, as described further below, or a number of other retention methods known in the art. Alternatively, components other than, or in addition to, the components of the needle assembly may be used to retain the needle. In at least one embodiment, the locking mechanism functions to retain the needle in a substantially fixed position while the barrel adapter and safety syringe are in a first stage, generally configured for drug injection. In at least one embodiment, the locking mechanism may include an interface on the barrel tip that engages the locking mechanism. Upon activation by the user, the needle hub may be employed to initiate the release of the locking mechanism from its engagement with the barrel tip. By releasing the locking mechanism from the barrel tip, the biasing member is allowed to expand causing the needle assembly to retract in the proximal direction substantially along a longitudinal axis of the barrel. In some embodiments of the present invention, the entire needle assembly is caused to retract, while in other embodiments only certain components thereof, including the needle, are caused to retract upon release of the locking mechanism and expansion of the proximally-biased biasing member. Similarly, in some embodiments of the present invention, the locking mechanism is caused to retract with the needle assembly, while in other embodiments the locking mechanism remains substantially stationary but enables the needle assembly, or components thereof, to move.

Accordingly, the barrel adapters include the components necessary for needle retention and retraction, and are configured to mate with standard barrels. The barrel adapter is configured to mate and be affixed, through a number of known methods, to the distal end of a barrel. In at least one embodiment, the barrel adapters are configured to mate with barrels that are substantially straight in cross-sectional profile (e.g., substantially parallel along at least a distal portion of the barrel), such as glass straight-barrels. The barrel adapters may be configured to mate with the barrel in a number of different ways. In a preferred embodiment, however, the barrel adapters are configured such that at least a proximal connecting portion is shaped to be mounted to and reside within the inner diameter of a distal portion of the barrel. As such, the barrel adapter may be connected to a standard straight-barrel drug chamber by being inserted into and attached, affixed, mounted, or otherwise mated to the distal end of the barrel. This enables the barrel adapters to be flexibly adaptable to barrels of all types, particularly standard glass straight-barrels, thereby providing potential manufacturing advantages and operational cost-savings. The barrel adapters of the present invention, therefore, simplify the assembly of needle retraction mechanisms with standard barrels to produce syringes with integrated needle safety features. In any of these embodiments of the barrel adapter, the biasing member is mounted, either fixedly or movably, generally within the barrel tip. The biasing member is biased to expand in the proximal direction and substantially along the longitudinal axis of the barrel.

The barrel adapters of the present invention enable selection and adaptation of varying needle assemblies with standard barrels. In other words, the design and configuration of the present invention allows a user to select a needle and/or needle assembly of a particular design or dimensions and adapt it to a syringe barrel for drug delivery. Accordingly, the barrel adapters of the present invention enable further customization of the drug delivery device by the user, allowing them to employ the integrated retraction mechanism of the barrel adapter to any barrel to produce a safety syringe. For example, the barrel adapters and needle assemblies may be configured to provide a number of different needle lengths. The user may then select the barrel adapter with their desired needle length and adapt it to a syringe to deliver the drug. This flexibility of the present invention is particularly useful for drug delivery that is subcutaneous or intramuscular. The barrel adapters of the present invention may be configured to enable such flexibility. One or more additional components may be utilized to provide this adaptive feature. For example, one or more connecting components may be utilized to connect the barrel tip of the barrel adapter to the barrel. In one such embodiment, one connecting component (such as a receiving component) may be fixedly mounted on a distal end of a glass barrel. The receiving component may directly receive and engage the barrel tip with the integrated retraction mechanism. Alternatively, the barrel adapter may include one or more additional connecting components (such as a mating component) which are used to engage the receiving component. Other optional components, such as elastomeric seals, which are known to one having ordinary skill in the art, may be necessary and incorporated into the device to facilitate the connection between the barrel adapter and the barrel.

Additionally, the barrel adapters of the present invention utilize materials that are substantially non-reactive with therapeutic fluids or drugs, and are suitable for use in pharmaceutical grade applications. The novel barrel adapters are configured to minimize or eliminate the possibility of contact or interaction between degradable materials, such as certain plastics, with the therapeutic fluids or drugs. The barrel adapters, with adaptable needle retention and retraction mechanisms, also provide fluid pathways from the primary drug chamber to the patient, through the needle, which are substantially absent of degradable materials. Such novel adapter configurations, when integrated into barrels to provide the novel safety syringes of the present invention, provide increased stability and shelf-life parameters to the drug and drug delivery devices. These characteristics are thought to be highly desirable for generally all pharmaceutical treatments, but may be of particular advantage in syringes for use with biologics and other complex therapies. In one embodiment, for example, a metal needle is retained within a glass barrel by an elastomeric needle seal at a proximal end of the needle and by an aperture of a plastic barrel tip at a portion of the needle that is distal to the needle seal, such that the drug fluid pathway contains (and the drug contacts) only glass, elastomer, and metal. In this way, the drug travels from drug chamber to patient without contacting any plastic. In other embodiments, other material combinations or fewer materials may be utilized for the drug fluid pathway.

Embodiments of the present invention also substantially reduce the number of components necessary for integrated needle retention and retraction mechanisms. In at least one embodiment of the present invention, for example, the barrel adapter does not require a conventional needle holder or needle-over-mold (e.g., a material that is formed over a needle to aid in the retention of the needle within the barrel for drug injection and to, alternatively or additionally, assist in the retraction of the needle after injection). Elimination of such components can further reduce the possibility of drug interaction with degradable materials, while also providing potential manufacturing advantages and operational cost-savings. The reduction of components in some embodiments of the present invention can be achieved by utilizing certain components for multiple functions.

In another embodiment, the present invention provides a safety syringe that includes a barrel, a plunger assembly, and a barrel adapter. The barrel adapter includes a barrel tip, a biasing member, a locking mechanism, and a needle assembly. The needle assembly may generally include a needle, a needle hub, and a needle seal. The needle is configured to pass-through the needle assembly, locking mechanism, biasing member, and barrel tip such that, one end the needle is within the barrel and another end the needle passes through an aperture in the barrel tip. The barrel may be substantially cylindrical, having along its longitudinal axis a distal end for drug injection, a proximal end for injection control, and at least a portion of the barrel interior for drug containment.

The barrel adapter is configured to mate and be affixed, through a number of known methods, to the distal end of a barrel. The barrel adapter is capable of coupling or mounting to, or engaging with, a barrel of the safety syringe. In any of these embodiments of the barrel adapter, the biasing member is mounted, either fixedly or movably, generally within the barrel tip and the distal end of the barrel. The biasing member is biased to expand in the proximal direction and substantially along the longitudinal axis of the barrel. The plunger assembly may include a plunger rod and a plunger stopper or seal. The plunger rod may be connected to the plunger seal by a number of different connections such as, for example, being screwed into the plunger seal. The plunger assembly may be mounted at the proximal end of the barrel while the barrel adapter is mounted at the distal end of the barrel. The plunger seal may comprise an elastomeric material and be sized such that it provides a compression fit with an inner diameter of the barrel such that it maintains a sterile drug chamber with container integrity. The plunger seal may also include an aperture, such as an axial pass-through, for example to enable removal of air from the drug chamber as the plunger seal is depressed into position within the barrel. The plunger seal aperture may be closed or capped by connection with the plunger rod, which may be screwed into the plunger seal aperture.

One or more embodiments of the present invention may optionally include certain standard components. For example, the barrel adapter configurations and syringe devices of the present invention may include one or more O-rings. In at least one embodiment, one or more O-rings are employed to seal the barrel tip within the barrel and/or to ensure a sterile environment and container integrity within the drug chamber of the barrel. Additionally or alternatively, the barrel adapter may include one or more controlling members to facilitate the control of the rate of retraction. Similarly, the barrel adapter may include one or more needle blocks, such as clips, flaps, flanges, or the like, which function to prevent the needle from being translated or protruding out of the barrel through the aperture of the barrel tip after the retraction mechanism has been initiated or completed. Furthermore, the safety syringe may include one or more components for aesthetics, ease-of-use, or other purposes. For example, one or more embodiments of the present invention may include a finger flange.

The novel barrel adapter designs of the present invention obviate the need to have a particular barrel shape or configuration for mounting a needle assembly thereto. Another desirable feature of the present invention is to provide a relatively simplified needle assembly which comprises fewer components, thereby providing a user-friendly and safe retractable syringe while keeping manufacturing costs to a minimum and/or facilitating mass distribution of retractable syringes. Embodiments of the present invention also provide configurations that allow the use of standard, commercially-available components, which may reduce overall manufacturing costs, streamline assembly processes, and avoid regulatory concerns often associated with non-standard materials and components. Additionally, the invention provides efficiently delivery of fluid contents, thereby minimizing wastage of fluid contents, and/or integrates one or more locking systems to prevent or at least minimize syringe re-use and/or needle stick injury.

Accordingly, in yet another embodiment the present invention provides a method for assembling a safety syringe having a barrel adapter, a plunger assembly, and a barrel having a longitudinal axis. The method includes the steps of: assembling the barrel adapter which includes a barrel tip, a biasing member, a locking mechanism, and a needle assembly; mounting the barrel tip to a distal end of the barrel; and mounting the plunger assembly having a plunger seal and a plunger rod to a proximal end of the barrel. The barrel adapter may be fixedly affixed, such as by glue, to the distal end of the barrel. The plunger assembly may be movably mounted to the distal end of the barrel by first inserting the plunger seal into the barrel and then inserting the plunger rod into the plunger seal by screw connection or another known method of connection. The method for assembling the safety syringe may further include the step of filling the barrel with a drug, after the step of mounting the barrel tip, but prior to the step of mounting the plunger assembly. In at least one embodiment, the barrel adapter is in a compressed configuration prior to mounting into the barrel. For example, the biasing member may be compressively engaged, such as in an energized stage, between the locking mechanism and the barrel tip prior to mounting the barrel adapter into the barrel. In another embodiment, these components may be mounted into the barrel prior to compressing and locking the biasing member into place. Accordingly, the method may further include the steps of compressing the biasing member and locking the locking mechanism into an engaged and energized position after the mounting of the barrel adapter to the barrel. It is contemplated that the plunger assembly may be utilized to compress the biasing member and lock the locking mechanism in some embodiments. In some embodiments, such as in a prefilled safety syringe configuration, at least part of the plunger assembly may then be removed to facilitate the filling process. For example, the plunger rod may be removed but the plunger seal may be retained in the barrel for the filling process. In other embodiments, such as in a fill-at-time-of-use configuration, the plunger assembly may be retained in the barrel of the safety syringe and drawn in the proximal direction to facilitate the filling of the barrel through the barrel adapter and, specifically, the needle assembly. As would be appreciated by an ordinarily skilled artisan, the drug may be a solution, a powder, a suspension, or the like, or any combination thereof.

In another embodiment the present invention provides a method of manufacturing a safety syringe which includes the steps of: mounting a retraction mechanism which includes a biasing member, a locking mechanism, and a needle assembly through a proximal end of a barrel, wherein a distal end of the retraction mechanism is axially translated to reside substantially within the barrel tip; and mounting the plunger assembly having a plunger seal and a plunger rod to a proximal end of the barrel. The plunger assembly may be movably mounted to the distal end of the barrel by first inserting the plunger seal into the barrel and then inserting the plunger rod into the plunger seal by screw connection or another known method of connection. The method for manufacturing the safety syringe may further include the step of filling the barrel with a drug, after the step of mounting the retraction mechanism but prior to the step of mounting the plunger assembly. The plunger seal may be mounted prior to, or in connection with, the plunger rod. In at least one embodiment, the retraction mechanism is in a compressed configuration prior to mounting into the barrel. For example, the biasing member may be compressively engaged, such as in an energized stage, prior to mounting the retraction mechanism into the barrel. In another embodiment, these components may be mounted into the barrel prior to compressing and locking the biasing member into place. In one such embodiment, the barrel tip is mounted to the distal end of the barrel while the remainder of the barrel adapter components are inserted through a proximal end of the barrel, axially translated within the barrel to the distal end of the barrel, and therein compressed and engaged to the barrel tip in an energized position. Accordingly, the method may further include the steps of compressing the biasing member and locking the locking mechanism into an engaged and energized position after the mounting of the retraction mechanism into the barrel.

A drug or pharmaceutical treatment may be filled in a portion of the barrel between the proximal end and the distal end constituting a drug chamber. The barrel adapter and the plunger assembly may be connected to the barrel by a number of known methods. For example, the barrel adapter may be fixedly attached, by a glue or other known method of adhesion or connection such as compression fit, to the distal end of the barrel. The syringe barrel may then be filled with a desired quantity of drug at the proximal end of the barrel. After completion of the filling, the plunger assembly may be mounted at the proximal end of the syringe barrel. As would be appreciated by one having ordinary skill in the art, this filling and assembly process may be completed under vacuum and/or a sterile environment to facilitate the aseptic manufacturing of the safety syringe. These safety syringes are configured such that they may readily be manufactured individually, or in a group, as is the case in a tray-based filling process.

In another embodiment, the present invention relates to a method of use for a safety syringe having a barrel adapter, a plunger assembly, and a barrel having a longitudinal axis. The barrel adapter, which may be mounted to a distal end of the barrel, includes a barrel tip, a biasing member such as a compression spring, a locking mechanism, and a needle assembly; wherein the components of the barrel adapter reside substantially within the barrel tip and the distal end of the barrel. The plunger assembly, which may be mounted to a proximal end of the barrel, includes a plunger seal and a plunger rod. The barrel adapter may be fixedly affixed, such as by glue, to the distal end of the barrel. The plunger assembly may be movably mounted to the distal end of the barrel by first inserting the plunger seal into the barrel and then inserting the plunger rod into the plunger seal by screw connection or another known method of connection. A drug may be contained within a portion of the barrel referred to as a drug chamber. The drug may be prefilled into the barrel during the manufacturing and filling process or filled at time-of-use or just prior to time-of-use. The method of use includes the steps: depressing the plunger assembly to facilitate delivery of a drug from the barrel; upon completion of the drug delivery, triggering the locking mechanism to release the biasing member from its energized state; and, by contact between the biasing member and the needle assembly, causing the needle assembly to retract into the barrel. In at least one embodiment, the locking mechanism may include an interface on the barrel tip which engages the locking mechanism. Upon activation by the user, the needle hub may be employed to initiate the release of the locking mechanism from its engagement with the barrel tip. By releasing the locking mechanism from the barrel tip, the biasing member is allowed to expand causing the needle assembly to retract in the proximal direction substantially along a longitudinal axis of the barrel. In some embodiments of the present invention, the entire needle assembly is caused to retract, while in other embodiments only certain components thereof, including the needle, are caused to retract upon release of the locking mechanism and activation of the biasing member. Similarly, in some embodiments of the present invention, the locking mechanism is caused to retract with the needle assembly while in other embodiments the locking mechanism remains substantially stationary but enables the needle assembly, or components thereof, to move.

Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, embodiments of the present invention may include one or more additional components which may be considered standard components in the industry of medical devices. The components, and embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein:

FIG. 3a shows an enlarged side view of a barrel adapter according to one embodiment of the present invention;

FIG. 3b shows a transparent side view of the barrel adapter of FIG. 3a;

FIG. 3c shows a partially exploded side view of the barrel adapter of FIG. 3a, separating the needle assembly from the other components of the barrel adapter;

FIG. 3d shows a fully exploded side view of the barrel adapter of FIG. 3a;

FIG. 4 shows an isometric view of a locking mechanism, according to an embodiment of the present invention;

FIG. 5 shows an isometric view of a barrel tip with an optional O-ring, according to an embodiment of the present invention;

FIG. 6 shows a needle seal and needle hub, according to an embodiment of the present invention;

FIG. 7 shows an optional needle block clip, according to an embodiment of the present invention;

DETAILED DESCRIPTION OF THE INVENTION

Figure 1:
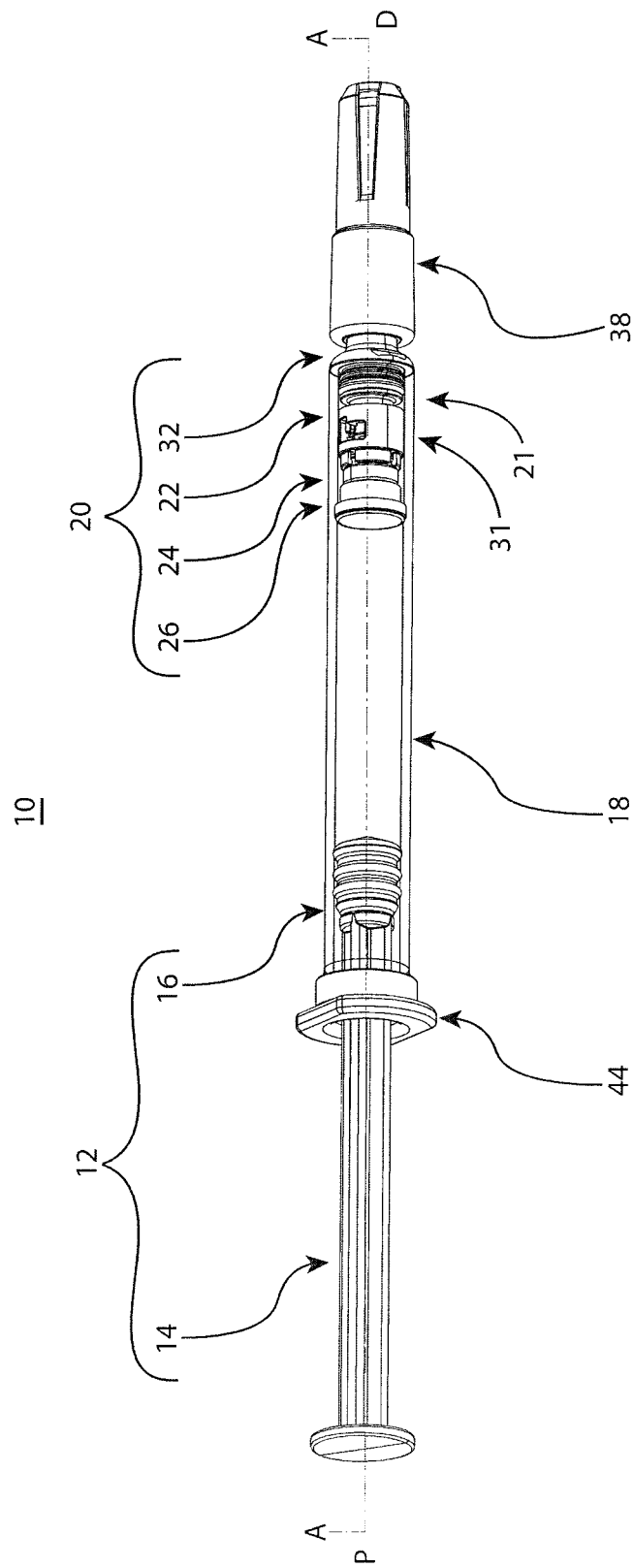
FIG. 1 is an isometric view of a first embodiment of a safety syringe according to the present invention.

The embodiments of the present invention provide reliable needle retraction, for improved user safety, without requiring complex manufacturing processes or operational changes for pharmaceutical companies or contract drug fillers. The embodiments of the present invention provide for a relatively simplified needle assembly which comprises fewer components, thereby providing a user-friendly and safe retractable syringe while keeping manufacturing costs to a minimum and/or facilitating mass distribution of retractable syringes. The novel barrel adapters of the present invention are notably able to be adapted to primary drug barrels of varying configurations and materials such as, preferably, straight-barrel glass barrels to provide integrated needle assemblies and retraction mechanisms to the barrel. Such embodiments may be utilized for pre-filled or fill at time-of-use injectable drug syringes. As such, the adaptable retraction mechanisms of the present invention may be flexibly attached, affixed, mounted, or otherwise mated to standard barrels, such as straight-glass barrels. The barrel adapters may be configured to mate with the barrel in a number of different ways, however, in a preferred embodiment, the barrel adapters are configured such that at least a proximal connecting portion is shaped to be mounted to, and reside within, the inner diameter of a distal portion of the barrel. As such, the barrel adapter may be connected to a standard straight-barrel drug chamber by having at least a proximal portion of the adapter inserted into and attached, affixed, mounted, or otherwise mated to the distal end of the barrel. The novel barrel adapter designs of the present invention therefore obviate the need to have a particular barrel shape or configuration for mounting a needle assembly thereto. This may substantially reduce manufacturing costs, especially those associated with the manufacture of specifically tailored glass barrels. The novel barrel adapters of the present invention can be mounted to, for example, straight glass barrels thereby simplifying the manufacturing process and costs associated with the manufacture of more complex barrel shapes.

The barrel adapters of the present invention may be selectable at the time of use or pre-attached to the barrel during manufacturing. In the selectable option, the design and configuration of the present invention allows a user to select a needle and/or needle assembly of a particular design or dimensions and adapt it to a syringe barrel for drug delivery. For example, the barrel adapters and needle assemblies may be configured to provide a number of different needle lengths or thicknesses. The user may then select the barrel adapter with their desired needle dimensions and adapt it to a syringe to deliver the drug. In the embodiments shown in FIGS. 1 and 2, the barrel adapter is directly mounted to the barrel. One or more additional components may be utilized to provide this adaptive feature. For example, one or more connecting components may be utilized to connect the barrel tip of the barrel adapter to the barrel. In one such embodiment, one connecting component (such as a receiving component) may be fixedly mounted on a distal end of a glass barrel. The receiving component may directly receive and engage the barrel tip with the integrated retraction mechanism. Alternatively the barrel adapter may include an additional connecting component (such as a mating component) which is used to engage the receiving component. Other optional components, such as elastomeric seals, which are known to one having ordinary skill in the art, may be necessary and incorporated into the device to facilitate the connection between the barrel adapter and the barrel. The barrel adapters, while including essentially the same components regardless of needle dimensions, may be customized to facilitate the complete retraction of the needle into the barrel. For example, longer biasing members (e.g., longer springs) may necessarily be selected or modified to facilitate retraction of a longer needle, as would be readily appreciated by one ordinarily skilled in the art.

The embodiments of the present invention provide configurations which may also utilize materials and components which are readily employable for pharmaceutical use, many of which are increasingly considered off-the-shelf or standard components. This reduces overall manufacturing costs, streamlines assembly processes, and avoids unnecessary regulatory concerns often associated with the use of non-standard materials and components. Additionally, the present invention provides components and devices which are aesthetically-similar to conventional syringes, which do not have needle retraction mechanisms, are ergonomically attractive to end-users, such as a medical practitioners and self-administering patients, and provide highly desired integrated safety features. These embodiments, accordingly, provide novel and cost-efficient components and devices which are readily integrated into drug filling processes.

Furthermore, the embodiments of the present invention provide efficient delivery of fluid contents, thereby minimizing wastage of pharmaceutical drugs. They similarly provide configurations which minimize dead-space, e.g., interstitial voids within the syringe barrel, which reduces or eliminates the capture of undesirable air bubbles during the assembly or filling process. These aspects of the present invention may provide highly desired functional and aesthetic characteristics, and may be modified to produce a range of different configurations.

For example, the embodiments of the present invention may utilize a flared needle, i.e., a needle that is flared at its proximal end to reduce the dead-space within the drug chamber of the barrel. The flaring of the needle may be configured to be a line-to-line fit with the distal face of the needle seal, or an interference fit with that surface. Because of this configuration, minimal or no dead-space is created between the needle and the needle seal, which provides improved accuracy of drug filling and dose delivery. This configuration of the present invention also greatly simplifies manufacturing processes. The needle seal may be pre-drilled to accept the needle or may be pierced by the needle at assembly. In either of these configurations, there are no additional components necessary to mate the needle to the needle seal or enable any of the features of the barrel adapter, retraction mechanism, or safety syringe.

The syringes of the present invention enable drug delivery with integrated safety as they prevent accidental exposure to the needle, as is common with needle stick injuries. As described above and detailed in the figures, a user may utilize the safety syringes of the present invention to perform the stages of drug delivery, including: needle injection, drug dose delivery, retraction activation, and needle retraction. Notably, the components of the barrel adapters of the present invention are held substantially in position through the stages of needle injection and drug dose delivery. This novel feature enables the barrel to be graduated, i.e., marked with volumes, because the reference point for end of dose is constant. The substantially stable and constant position of the needle seal through the stages of needle injection and dose delivery, the stages during which some amount of drug may still reside in the drug chamber of the barrel, enables the identification of "zero volume," i.e., the point where there is no drug left in the chamber. Moving proximally from this point along the axial length of the barrel, drug volumes can be calculated based on the diameter of the barrel and can be marked along the length of the barrel. Several methodologies exist for measuring volumes and marking graduations on cylindrical barrels, which are known to one having ordinary skill in the art. Accordingly, the novel design of the barrel adapters and syringes of the present invention enable the use of graduated syringe barrels. This is a desirable feature for syringe users, including medical professionals and patients.

By integrating one or more locking systems to prevent or at least minimize syringe re-use and/or needle stick injury, the embodiments of the present invention provide highly desirable products which are cost-efficient to manufacture and easy-to-use by medical practitioners and self-administering patients. Such locking systems may include, for example, needle retraction mechanisms and/or arrangements that block a retracted needle from again extending from the end of the syringe. The novel features and functionality of the barrel adapters and syringes of the present invention provide a number of safety advantages to the user. For example, the locking mechanism may be configured to provide visual, audible, and/or tactile feedback to the user that the drug dose has been fully delivered, the retraction mechanism has been activated, the needle has been retracted, and that the syringe is safe for disposal. The components of the present invention are also configured such that there is increased destruction of the components, and the syringe overall, at the end of use. Such integrated safety and destruction prevents the reusability of the syringe and increases the safety profile of the device. For example, an optional needle block may be configured to prevent the needle from translating in the proximal direction out of the barrel tip after needle retraction. Depression of the plunger rod and axial translation of the needle in the proximal direction, in this configuration, will result in the needle becoming bent within the barrel as a force is applied by the user. Another safety feature enabled by the present invention is the ability to control the rate of retraction of the needle. Controlled needle retraction prevents injury to the patient after the drug dose has been delivered. This can be facilitated by active components, such as one or more friction members limiting the rate of expansion of the biasing member upon retraction activation, or by passive components, such as the selection of biasing members which have slower expansion. In the embodiments shown in FIGS. 1 and 2, the retraction is controlled by plunger rod and plunger seal. At the end of dose, upon activation of needle retraction, the user is still in contact and applying force to the proximal end of the plunger rod. As the biasing member is caused to expand, it imposes an axial force in the proximal direction to retraction the needle and/or needle assembly. This action conveys the force to the plunger seal, which is in contact with the needle seal at the end of dose, and the plunger rod. The friction caused by the needle seal and the plunger seal against the interior of the barrel limits the rate of retraction of the needle assembly. As the user reduces the force they apply on the plunger rod, they can also control the rate of needle retraction. This controlled retraction is highly desired by syringe users as it increases the safety and reduces the pain felt to the patient.

The embodiments of the present invention are detailed further herein with respect to the attached figures. It is to be understood that these are merely non-limiting embodiments and that other similar embodiments are within the contemplation of the present invention and within the breadth and scope of the present disclosure.

As used herein to describe the syringe, barrel, barrel adapter, or any of the relative positions of the components of the present invention, the terms "axial" or "axially" refer generally to a longitudinal axis "A" around which syringe or barrel is preferably formed although not necessarily symmetrically there-around. The term "radial" refers generally to a direction normal to the axis "A". The terms "proximal," "rear," "rearward," "back," or "backward" refer generally to an axial direction away from barrel tip 32. The terms "distal," "front," "frontward," "depressed," or "forward"

refer generally to an axial direction towards the barrel tip 32. It is to be understood that the term "spring" is used herein to suggest a biasing member, such as a substantially spiral-wound coil, that may be compressed and allowed to expand in a given direction. While the spring element such as the arrangement discussed and utilized in the embodiments detailed herein may be utilized, it is within the contemplation of the present invention that other types of biasing members may be readily employed for the same purpose while remaining within the breadth and scope of the present invention. For example, springs such as compression springs, torsion springs, constant force springs, extension springs, and leaf springs, or combinations of different types of springs may be utilized within the scope of the present invention, as would be understood by an ordinarily skilled artisan. Additionally or alternatively, biasing members other than springs may also be employed for similar purposes. Non-limiting examples of biasing members include a spring, elastic or other device for storing releasable energy. In at least one embodiment, however, the biasing member is preferably a spring, such as a compression spring.

As used herein, the term "glass" should be understood to include other similarly non-reactive materials suitable for use in a pharmaceutical grade application that would normally require glass. The term "plastic" may include both thermoplastic and thermosetting polymers. Thermoplastic polymers can be resoftened to their original condition by heat; thermosetting polymers cannot. As used herein, the term "plastic" refers primarily to moldable thermoplastic high polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" does not include either glass or rubbery elastomers that are approved for use in applications where they are in direct contact with therapeutic liquids that can interact with plastic or that can be degraded by substituents that could otherwise enter the liquid from plastic. As used herein, the term "elastomer," "elastomeric" or "elastomeric material" refers primarily to crosslinked thermosetting rubbery polymers that are more easily deformable than plastics but that are approved for use with pharmaceutical grade fluids and are not readily susceptible to leaching or gas migration. As used herein, the term "fluid" refers primarily to liquids, but can also include suspensions of solids dispersed in liquids, and gasses dissolved in or otherwise present together within liquids inside the fluid-containing portions of syringes.

Additionally, the barrel adapters of the present invention utilize materials that are substantially non-reactive with therapeutic fluids or drugs, and are suitable for use in pharmaceutical grade applications. The novel barrel adapters are configured to minimize or eliminate the possibility of contact or interaction between degradable materials, such as certain plastics, with the therapeutic fluids or drugs. The barrel adapters, with adaptable needle retention and retraction mechanisms, also provide fluid pathways from the primary drug chamber to the patient, through the needle, which are substantially absent of degradable materials. Such novel adapter configurations, when integrated into barrels to provide the novel safety syringes of the present invention, provide increased stability and shelf-life parameters to the drug and drug delivery devices. These characteristics are thought to be highly desirable for generally all pharmaceutical treatments, but perhaps especially of value in syringes for use with biologics and other complex therapies. In one embodiment, for example, a metal needle is retained within a glass barrel by an elastomeric needle seal at a proximal end of the needle and by an aperture of a plastic barrel tip at a portion of the needle that is distal to the needle seal, such that the drug fluid pathway contains (and the drug contacts) only glass, elastomer, and metal, without contacting any plastic, as the drug travels from drug chamber to patient. In other embodiments, other material combinations or fewer materials may be utilized for the drug fluid pathway.

One or more embodiments of the present invention may further include certain standard components. For example, the barrel adapter configurations and syringe devices of the present invention may include one or more O-rings. In at least one embodiment, one or more O-rings are employed to seal the barrel tip within the barrel and/or to ensure a sterile environment and container integrity within the drug chamber of the barrel.

Additionally or alternatively, the barrel adapter may include one or more controlling members to facilitate the control of the rate of retraction. Similarly, the barrel adapter may include one or more needle blocks, such as clips, flaps, flanges, or the like, which function to prevent the needle from being translated or protruding out of the barrel through the aperture of the barrel tip after the retraction mechanism has been initiated or completed.

Furthermore, the safety syringe may include one or more components for aesthetics, ease-of-use, or other purposes. For example, one or more embodiments of the present invention may include a finger flange. The finger flange may be pre-formed along any portion of the barrel or safety syringe, or may be a separate component that is connected to or affixed to the barrel or safety syringe. In at least one embodiment, the finger flange is a preformed component at the proximal end of the barrel. The finger flange may be configured to allow a user to rest their pointer and middle fingers on the flange, and may provide a leverage interface when the user is depressing the plunger with their thumb for injection of the drug. The position, shape, number, and materials for such components may vary, as would be readily appreciated by a skilled artisan, to meet any number of desired characteristics.

Similarly, while the components of the barrel adapter and the safety syringe are described herein as separate components, it is within the contemplation of the present invention that certain groups of these components may be combined to form a single component capable of performing the functions of the individual components. As described above, for example, in at least one embodiment the needle hub and needle seal may be one unified component that provides a dual function. Additionally, as would be appreciated by one having ordinary skill in the art, the components of the safety syringes may be manufactured as individual components or as single components. As described above, the finger flange may be a component that is pre-formed, during the manufacturing process, as a part of the barrel itself. Accordingly, in at least one embodiment, the finger flange may be a glass finger flange extension of the barrel.

Furthermore, while the components of the barrel adapter are described herein as separate components, they may be unified components having multiple functions. As discussed above, the biasing member (e.g., spring) may be compressed in its energized state and the locking mechanism engaged either prior to installation in the barrel tip or after the components have been mounted in the barrel. The configuration of the components and their assembly may vary based on the assembly process, the device parameters, and other desired characteristics.

Figure 2:
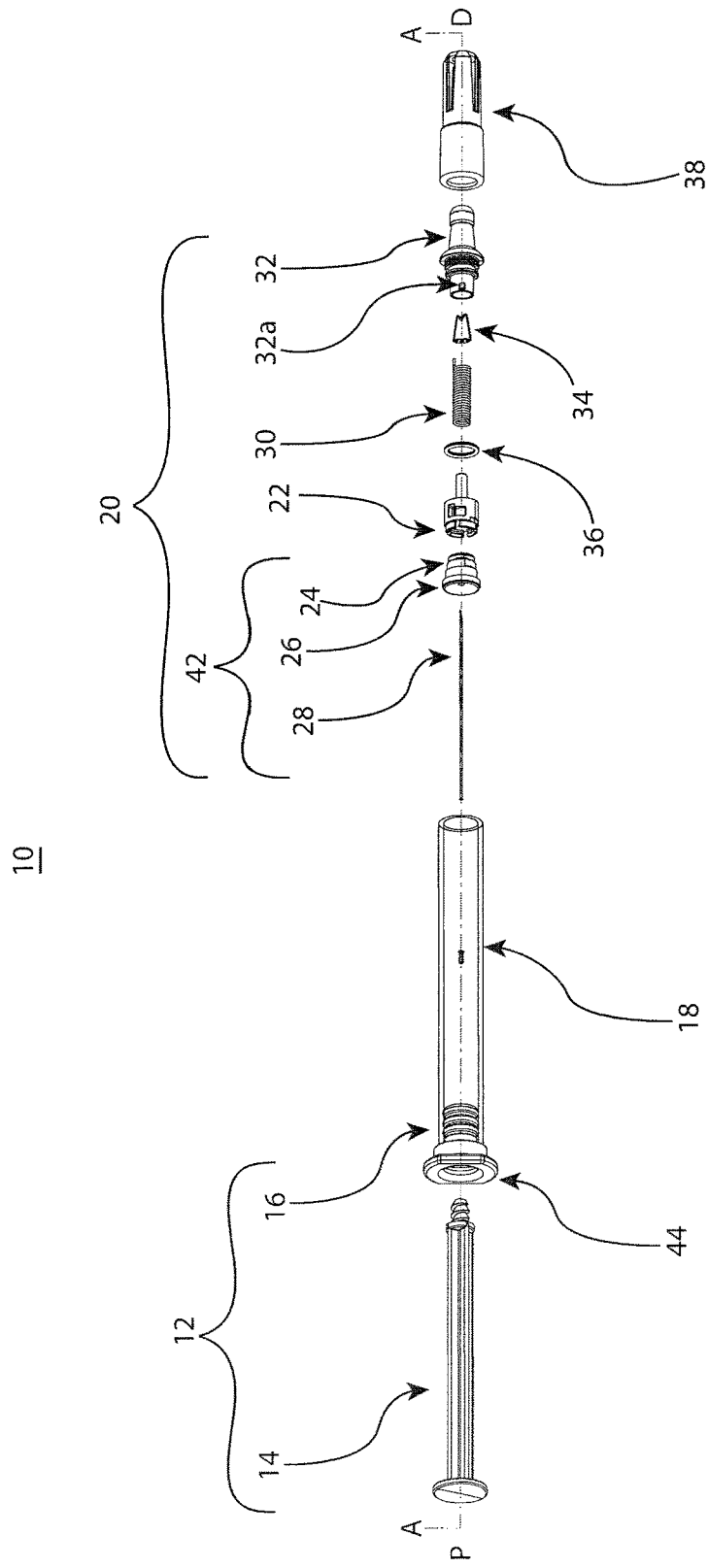
FIG. 2 is an exploded view, along a longitudinal axis, of the embodiment shown in FIG. 1.

FIG. 1 shows an isometric view of one embodiment of a safety syringe 10, according to the present invention. FIG. 2 shows an exploded view of the safety syringe 10, and its components, shown in FIG. 1. In accordance with the invention, a barrel adapter 20 is provided for attachment to a syringe barrel 18 having a plunger assembly 12. As an advantage of the embodiments of the present invention, the barrel tip 32 of the barrel adapter 20 may be configured to mate with any standard barrel 18 by any appropriate method. The barrel 18 may be a plastic barrel, a glass barrel, or made of any other known material for use in medical devices. The barrel 18 may be tapered, non-cylindrical, or substantially straight. In an embodiment preferred for manufacturing purposes, the barrel 18 is a straight barrel glass cylinder. The embodiments of the present invention also enable significant other advantages in the marketplace for safety syringes.

For example, one or more embodiments can utilize standard components, such as standard plunger rods, plunger seals, and rigid needle shields, thereby greatly reducing the need for specially-tailored or injection molded components. For example, FIGS. 1-2 show an embodiment which utilizes a standard plunger rod 14, plunger seal 16, and a rigid needle shield 38, among other possible standard components. The plunger seal 16 may be, for example, an ethylene tetrafluoroethylene (ETFE) coated rubber stopper/seal, such as that which is readily-available under the trade name "FluroTec" from West Pharmaceutical Services, Inc., of Lionville, Pa. Other components may similarly be standard, off-the-shelf components, providing a great advantage of the embodiments of the present invention. This advantage of the embodiments of the present invention provides valuable manufacturing efficiencies and operational cost-savings.

The barrel adapter 20 may be mounted to the syringe barrel 18 by any appropriate coupling arrangement, as will be understood by those of skill in the art. For example, the barrel adapter 20 may be coupled to the syringe barrel 18 by a coupling structure that may be separate from components of the barrel adapter 20 and syringe barrel 18, or integral with the barrel adapter 20 and the syringe barrel 18. Moreover, the barrel adapter 20 may be coupled to the syringe barrel 18 during the syringe manufacturing process or just prior to use. By way of example only, the syringe adapter 20 may be coupled to the syringe barrel 18 by an interference fit, glue, or the like during the syringe manufacturing process. Alternately, for example, the syringe barrel 18 and barrel adapter 20 may include mating threads or a Luer locking arrangement, such that the barrel adapter 20 may be coupled to the syringe barrel 18 just prior to use.

The barrel adapter 20 facilitates mounting of a needle 28 (see FIG. 2) to the syringe barrel 18. The barrel adapter 20 includes a barrel tip 32, a needle assembly 42, and a needle retraction mechanism 21. The barrel tip 32 may be coupled to the syringe barrel 18 by any appropriate method, as explained above with regard to the attachment of the barrel adapter 20 to the syringe barrel 18. The barrel tip 32 typically presents a distal end to the safety syringe 10 when coupled to the syringe barrel 18, the needle 28 extending through the distal end of the barrel tip during injection of a medicament. The barrel tip 32 may further include structure that forms a part of the needle retraction mechanism 21, as will be explained below.

The needle assembly 42 may generally include a needle 28, a needle hub 24, and a needle seal 26. The needle 28 is configured to pass-through the needle hub 24 and needle seal 26 of the needle assembly 42, as well as the locking mechanism 22, spring 30, and barrel tip 32 such that, one end the needle 28 is within the barrel 18 and another end the needle 28 passes through an aperture in the barrel tip 32. In some embodiments, the needle hub 24 and needle seal 26 may be one component, while in other embodiments they may comprise two or more components. For example, in one embodiment the needle hub 24 and needle seal 26 are a unified unit such as a dual-shot plastic needle hub 24 and elastomeric needle seal 26.

The needle seal 26 and needle hub 24 may be configured to remain in a substantially fixed position within the barrel 18 while the needle assembly 42 is in a first stage, for injection of a drug to a patient. Alternatively, the needle seal 26 and needle hub 24 may be configured to move to an injection position, for example, as the plunger rod 14 is depressed.

In order to prevent inadvertent sticking with the needle 28 or reuse of the syringe 10 following administration of a medicament, the barrel adapter 20 includes the needle retraction mechanism 21. According to an aspect of the invention, actuation of the needle retraction mechanism 21 causes at least the needle 28 of the needle assembly 42 to retract into the barrel adapter 20 after delivery of a medicament through the needle 28. The needle retraction mechanism 21 includes a biasing member 30 and an actuable locking arrangement 31 that maintains the biasing member 30 in an energized position until such time as the needle 28 of the needle assembly 42 is retracted into the barrel adapter 20. While the locking arrangement 31 may be any appropriate design that maintains the biasing member 30 in an energized position until such time as the needle 28 is to be retracted, in the illustrated embodiment, the locking arrangement 31 includes a locking mechanism 22 and locking aspects 32a that mate to maintain the relative positions of surfaces that maintain the biasing member 20 in an energized position, as will be explained in greater detail below. Upon actuation of the locking arrangement 31, the biasing member 30 causes the needle 28 to retract into the barrel adapter 20.

In one such embodiment of a locking arrangement 31, the biasing member 30 is a compression spring. Ends of the spring 30 are disposed adjacent surface 23 of the locking mechanism 22 and surface 25, within the barrel tip 32. The relative positions of the surfaces 23, 25 maintain biasing member 30 is maintained in the compressed, energized position prior to injection, or allow the spring 30 to move to a deenergized position to retract the needle 28 following injection. In order to maintain the spring 30 in an energized position, the locking mechanism 22 and the barrel tip 32 include mating structure that may be decoupled to allow the spring 30 to move to a deenergized position.

The needle retraction mechanism 21 may be actuated by any appropriate trigger. For example, in the illustrated embodiment, the needle retraction mechanism 21 is actuated by movement of the plunger seal 16 into contact with the needle assembly 42. In such a configuration, the needle hub 24 may be forced into contacting and/or depressing on the locking mechanism 22. This contact may disengage the locking mechanism 22 allowing the spring 30 to expand in the proximal direction substantially along a longitudinal axis of the barrel 18, thereby causing the locking mechanism 22 and the components of the needle assembly 42, including the needle 28, to retract into the barrel 18.

In the illustrated mating structure of the needle retraction mechanism 21, the locking mechanism 22 is caused to engage and remain connected with one or more corresponding locking aspects 32a of the barrel tip 32. As the locking mechanism 22 is caused to translate in the distal direction, such as by contact by the needle hub 24 and through the force applied by the user to the plunger assembly 12, the locking mechanism 22 is allowed to disengage from the one or more corresponding locking aspects 32a of the barrel tip 32, allowing the spring 30 to expand and the retraction mechanism to activate. The disengagement of the locking mechanism 22 from the locking aspects 32a may be caused by axial translation of the locking mechanism 22. Additionally or alternatively, the disengagement of the locking mechanism 22 from the locking aspects 32a may be caused by rotation of the locking mechanism 22, such as rotation upon axial translation. The rotation, by itself or in conjunction with the axial translation, enables the locking mechanism 22 to escape from the engagement with the locking aspects 32a. In at least one embodiment, this rotation may be caused by a torsionally biased compression spring which rotates the locking mechanism 22 in one direction around the axis upon compression. In another embodiment, the rotation may be caused by a configuration of the locking mechanism 22 itself to enable this functionality, such as a pitched aspect profile of the locking mechanism 22, by a shaping of the locking aspects 32a, or by the interface between the locking aspects 32a and locking mechanism 22 which promote this movement and allow for the engagement and disengagement of the components.

The needle hub 24 may function to retain the needle 28 in a substantially fixed position while the barrel adapter 20 and safety syringe 10 are in a first stage, i.e., generally configured for drug injection. Additionally or alternatively, the locking mechanism 22 may function to retain the needle 28 in a substantially fixed position during this first stage for drug injection. As such, the safety syringe 10 shown in FIGS. 1-2 incorporates one embodiment of the novel barrel adapters which does not require a conventional needle holder or needle-over-mold (not shown). It will be understood by those of skill in the art that a conventional needle holder or need-over-mold may include, for example, a material that is formed over a needle to aid in the retention of the needle within the barrel 18 for drug injection and to, alternatively or additionally, assist in the retraction of the needle after injection. Elimination of such components can further reduce the possibility of drug interaction with degradable materials, while also providing potential manufacturing advantages and operational cost-savings.

Upon disengagement of the locking mechanism 22 and activation of the retraction mechanism, the spring 30 is allowed to expand causing the needle assembly 42 to retract in the proximal direction substantially along a longitudinal axis of the barrel 18. In some embodiments of the present invention, the entire needle assembly 42 is caused to retract, while in other embodiments only certain components thereof, including the needle 28, are caused to retract upon release of the locking mechanism 22 and expansion of the proximally-biased spring 30. Similarly, in some embodiments of the present invention, the locking mechanism 22 is caused to retract with the needle assembly 42 while in other embodiments the locking mechanism 22 remains substantially stationary but enables the needle assembly 42, or components thereof, to move. After retraction of the needle 28 has been initiated or completed, needle block 34 functions to prevent the needle 28 from translating in the distal direction and out of the barrel tip 32. As stated above, other standard components may be utilized in the assembly of the safety syringes, such as O-ring 36.

A drug or pharmaceutical compound may be contained in the barrel 18 proximally of the needle seal 26. As would be appreciated by an ordinarily skilled artisan, the drug may be a solution, a powder, a suspension, or the like, or any combination thereof. The needle hub 24 and needle seal 26 have an aperture pass-through at their center (e.g., at substantially the longitudinal axis of these components and the barrel 18). This aperture may have a diameter equal to the diameter of the needle 28, such that the needle 28 is retained in position within the needle hub 24 and/or needle seal 26 during an initial injection stage and allowed to axially translate in the proximal direction upon activation of the retraction mechanism, with or without the needle hub 24 and/or needle seal 26. Alternatively, the needle seal 26 may not initially have an aperture prior to positioning of the needle 28 within the needle seal 26 at assembly. In this configuration, the needle 28 may be pushed through the needle seal 26 at assembly and create a line-to-line or interference fit, thereby ensuring a tight seal between the components and minimal or no dead-space.

At the end of drug delivery, the force applied by the user to axially translate the plunger seal 16 and plunger rod 14 may be used to disengage the locking mechanism 22 and activate the retraction mechanism. For example, the plunger seal 16 may be made to contact the needle seal 26 such that force applied to the plunger rod 14 by a user is applied to the plunger seal 16 and transferred, at least in part, to the needle seal 26. The force imparted to the needle seal 26 may similarly be transferred, at least in part, to the needle hub 24. Through this transfer, a release ring component of the needle hub 24, or similar aspect thereof, may be caused to push upon or otherwise initiate the release of the locking mechanism 22 from the engaged connection with the locking aspects 32a of the barrel tip 32. By releasing the locking mechanism 22 from the locking aspects 32a of the barrel tip 32, the biasing member (e.g., spring) 30 is allowed to expand and retract the needle assembly 42 and needle 28 in the proximal direction substantially along a longitudinal axis of the barrel 18. In such embodiments of the present invention, only the needle 28, needle assembly 42, and locking mechanism 22 are caused to retract upon release of the locking mechanism 22 and expansion of the proximally-biased spring 30.

The embodiment shown in FIGS. 1-2 includes a configuration where the locking mechanism 22 is separate from the barrel tip 32. The locking mechanism, however, may be configured to be part of, or attached to, the barrel tip 32. As discussed above, the locking mechanism may be a separate component or a dual-purpose component, such as a dual purpose locking mechanism and needle block 34. In other words, the locking mechanism may contain or activate features that block the needle 28 from translating axially in the distal direction after the retraction mechanism has been activated and the needle has been retracted.

Alternatively, a separate needle block 34 component may be utilized as shown in the embodiment of FIGS. 3a-3d. For ease of explanation, like numbers are utilized in the explanation of the embodiment of FIGS. 3a-3d. FIG. 3a shows a barrel adapter 20, according to one embodiment of the present invention, which includes a barrel tip 32, a needle block 34, an O-ring 36, a locking mechanism 22, a needle seal 26, a needle hub 24, and a needle 28, as may be seen in FIG. 3b, which shows a transparent view of the barrel tip 32 shown in FIG. 3a. Many of these components are housed or reside at least partially within the barrel tip 32. As can be seen in FIG. 3b, the biasing member 30 resides at least partially within the barrel tip 32. When in the compressed state, the biasing member 30 resides within the barrel tip 32 at a distal end and with the locking mechanism 22 at a proximal end. The components of the barrel adapter 20 are shown in a partially exploded view in FIG. 3c, and in a fully exploded view in FIG. 3d. The needle assembly 42, which includes needle seal 26, needle hub 24, and needle 28, may be assembled separately from, or together with, the other components of the barrel adapter 20. For example, all of the components may be pre-assembled into a complete barrel adapter 20, as illustrated in FIG. 3a, for mating into a barrel, such as the barrel 18 illustrated in FIGS. 1 and 2. Alternatively, the components of the needle assembly 42 may be assembled separately from the remaining components of the barrel adapter 20. In this second configuration, the needle assembly 42 may be mounted into the barrel 18 from the proximal end during assembly instead of at the distal end with the barrel adapter 20.

FIGS. 4-7 show the components of the barrel adapter 20 separately, excluding the needle 28. FIG. 4 shows a locking mechanism 22 according to one embodiment of the present invention. FIG. 5 shows the barrel tip 32. The barrel tip 32 has locking aspects 32a, which are engageable with receiving structures of the locking mechanism 22. In this embodiment, the barrel tip 32 has two locking aspects 32a which engage with corresponding locking portals in the locking mechanism 22. It will be appreciated, however, that the barrel tip 32 may have one or more locking aspects.

As shown in FIG. 4, the receiving structures of the locking mechanism 22 may be, for example, in the form of locking portals 46. In the illustrated embodiment, the locking portals 46 are "L" shaped cutouts. One or more channels 47 within the inner diameter of the locking mechanism 22 permit the locking aspects 32a to slide into the locking portals 46 and, upon rotation of the locking mechanism 22, sit at rest within seats 22a of the locking portals 46 of the locking mechanism 22. In this way, the relative positions of locking mechanism 22 and the barrel tip 32 are maintained as the biasing member 30 of this embodiment biases the locking mechanism 22 and the barrel tip 32 apart. While the locking mechanism 22 and the barrel tip 32 of the illustrated embodiment include the locking portals 46 and locking aspects 32a, respectively, it will be appreciated that the locking mechanism 22 and barrel tip 32 could alternately include the locking aspects 32a and the locking portals 46, respectively, so long as the engagement provides an arrangement that is operable to engageably/releasably couple the associated components. It will further be appreciated that the locking mechanism may be of an alternate structure entirely, so long as the arrangement provides for the retractable disposition of the needle 28 within the syringe, actuable upon activation as a result of depression of the plunger rod 14.

In order to unlock the locking mechanism 22 and the barrel tip 32 in the illustrated embodiment, in addition to biasing the locking mechanism 22 and the barrel tip 32 apart, the biasing member 30 provides a relative torsional rotation between the locking mechanism 22 and the barrel tip 32. Such torsional rotation is enabled by the axial motion of the plunger seal 16 on the locking mechanism 22 during, or at the end of, drug administration. In this regard, the compression spring 30 is not only held in compression by the engagement between the locking mechanism 22 and the barrel tip 32, the spring 30 is additionally held in an energized torsional position, i.e., it is also mounted as a torsionally-biased compression spring. Referring to FIG. 3C, the spring 30 includes end 30a, which extends generally radially, and end 30b, which extends generally longitudinally. The ends 30a, 30b engage the locking mechanism 22 and the barrel tip 32, which are held in position relative to one another with the locking aspects 32a engaging seat 22a of the locking portals 46. As may be seen in FIG. 3B, end 30b is received in a slot 33 in barrel tip 32. Although not visible in the figures, end 30a similarly engages locking mechanism 22. In this way, when the movement of the plunger seal 16 in conjunction with the outward biasing force of the spring 30 unseats locking aspects 32a from seat 22a, the spring 30 causes the locking mechanism 22 to rotate relative to the locking aspects 32 of the barrel tip 32. When the locking aspects 32a reach the slots 47 (see FIG. 4), the continued outward biasing force of the spring 30 causes the locking element 22 to unlock from the barrel tip 32.

In other words, as the locking mechanism 22 is depressed by the activation force applied by the user on the plunger rod 14 at the end of drug dose delivery, the retraction mechanism is activated. This means that the locking mechanism 22 is permitted to rotate by the torsional bias of the spring 30. This torsional rotation of the locking mechanism 22 aligns the locking aspects 32a with the one or more channels and permits the locking mechanism 22 to disengage from the locking aspects 32a. The biasing member or spring 30 is permitted to expand in the proximal direction once this alignment of the locking aspects 32a with the one or more channels occurs, thereby causing retraction of the needle 28 from the barrel tip 32.

It will be appreciated that the locking mechanism 22 is permitted to freely rotate, upon retraction activation by the user, inasmuch as there is minimal friction between the locking mechanism 22 and the needle hub 24 (shown in FIG. 6). As discussed above, the needle seal 26 and needle hub 24, may be separate components or a dual-shot singular component. In at least one embodiment, the needle seal 26 and needle hub 24 are separate components to ensure that minimal surface friction is present between the needle hub 24 and the locking mechanism 22 to allow for substantially free rotation of the locking mechanism 22 upon retraction activation.

According to another aspect of the invention, in some embodiments, following retraction of the needle 28, the barrel adapter 20 may be provided with a block that prevents or inhibits the needle 28 from again protruding from the barrel tip 32. FIG. 7 shows one embodiment of a needle block 34, which may reside within the distal end of the barrel tip 32. The illustrated needle block 34 includes a flange 48 having a central aperture 50 for passage of the needle 28. A pair of anus 52 extends from the flange 48, the distal ends of the arms 52 supporting a pair of clips 54. When the needle block 34 is disposed within the barrel tip 32, the anus 52 bias the clips 54 toward one another. In this embodiment, with the needle 28 extending through the aperture 50 of the flange 48, the clips 54 at the distal end of the needle block 34 expand and permit disposition of the needle 28 between the clips 54 when the needle 28 is in the injection and retraction stages. Upon retraction of the needle 28 in the proximal direction past the clips 54, however, the arms 52 bias the clips 54 to a closed position and do not permit the needle 28 to pass-through in the distal direction. While the assembly may be alternately configured, in this embodiment, a distal end of the biasing member or spring 30 may be disposed adjacent the flange 48 during assembly. It will be appreciated that the needle block 34 illustrated is disclosed by way of example only, and the block may be of an alternate configuration and structure.

The embodiments of the present invention also provide configurations which allow the use of standard, commercially-available components, thereby reducing overall manufacturing costs, streamlining assembly processes, and avoiding regulatory concerns often associated with non-standard materials and components. For example, the barrel may be made of certain plastics, glass, or any other material commonly used for medical grade products. One or more components of the present invention may also be made up of certain plastics, such as the polycarbonate plastics sold under the trade name "LEXAN" by SABIC Innovative Plastics of Pittsfield, Mass. Similarly, certain elastomeric polymers or rubbers may be utilized, such as the rubber products sold under the trade name "HELVOET" by Datwyler Pharma Packaging USA Inc. of Pennsauken, N.J., for components such as the needle seal 26 and the plunger seal 16. Various medical grade metals, such as stainless steel, may be utilized for the needle 28, as would be appreciated by an ordinarily skilled artisan. These components, the barrel adapters 20, and the safety syringes 10 may be shaped or sized in a myriad of different configurations to meet the desired parameters. These components, barrel adapters 20, and syringes 10 may be assembled, and/or filled with a drug, by a multitude of processes known in the art. For example, well known glues or welding methods such as ultrasonic welding may be employed to assemble the components of the present invention.

The novel barrel adapter and syringe designs of the present invention enable relatively simplified needle assembly 42 and filling processes. One method for assembling a safety syringe having a barrel adapter 20, a plunger assemble 12, and a barrel 18 having a longitudinal axis includes the steps of: assembling the barrel adapter 20 which includes a barrel tip 32, a spring 30, a locking mechanism 22, and a needle assembly 42; mounting the barrel tip 32 to a distal end of the barrel 18; and mounting the plunger assemble 12 having a plunger seal 16 and a plunger rod 14 to a proximal end of the barrel 18. The barrel adapter 20 may be fixedly mounted, such as by glue, to the distal end of the barrel 18. The plunger assemble 12 may be movably mounted to the distal end of the barrel 18 by first inserting the plunger seal 16 into the barrel 18 and then inserting the plunger rod 14 into the plunger seal 16 by screw connection or another known method of connection. The method for assembling the safety syringe may further include the step of filling the barrel 18 with a drug, after the step of mounting the barrel tip 32 but prior to the step of mounting the plunger assemble 12.

The plunger seal 16 may comprise of an elastomeric material and be sized such that it provides a compression fit with an inner diameter of the barrel 18 in order to maintain the sterility and container integrity of the drug chamber. The plunger seal 16 may also include an aperture, such as an axial pass-through, for example to enable removal of air from the drug chamber as the plunger seal 16 is depressed into position within the barrel 18. Accordingly, the drug may be filled into the barrel 18 prior to mounting of the plunger assemble 12, or just prior to mounting of the plunger seal 16. In the latter configuration, the plunger seal 16 may be slide into position in contact with the drug fluid in a sterile environment or other aseptic conditions. The plunger seal 16 aperture allows for residual air bubbles, if any, to escape the drug chamber when the plunger seal 16 is pushed into contact with the fluid. Subsequently, the plunger seal aperture may be closed or capped by connection with the plunger rod 14, which may be screwed into the plunger seal aperture. The syringe, which may be considered a prefilled syringe, is then ready for use. Alternatively, the components of the present invention may be assembled without the drug filling step, such as in a fill at time-of-use process. In one such process, the drug may be filled by backwards drawing the plunger rod 14 and plunger seal 16 while the needle 28 is aseptically connected to a drug vial. In this manner, the drug fluid is pulled by vacuum action into the drug chamber through the needle 28.

In at least one embodiment, the barrel adapter 20 is in a compressed configuration prior to mounting into the barrel 18. For example, the biasing member (e.g., spring 30) may be compressively engaged, such as in an energized stage, between the locking mechanism 22 and the barrel tip 32 prior to mounting the barrel adapter 20 into the barrel 18. In another embodiment, these components may be mounted into the barrel 18 prior to compressing and locking the spring 30 into place. Accordingly, the method may further include the steps of compressing the spring 30 and locking the locking mechanism 22 into an engaged and energized position after the mounting of the barrel adapter 20 to the barrel 18. It is contemplated that, in at least one embodiment, the plunger assemble 12 may be utilized to compress the spring 30 and lock the locking mechanism 22. For example, prior to filling a drug into the drug chamber, the plunger seal 16 and plunger rod 14 may be used to push the needle hub 24, needle seal 26, needle 28, biasing member, and locking mechanism 22 into place substantially within the barrel tip 32 and the distal end of the barrel 18, in locked engagement with the one or more corresponding locking aspects 32a of the barrel tip 32. Needle 28, needle seal 26, and needle hub 24 may be pushed into place either separately from or together with the other components of the device. The plunger rod 14, and optionally plunger seal 16, may then be removed from the barrel 18 to facilitate the filling process, as may be the case for a prefilled syringe filling process. Alternatively the plunger rod 14 and plunger seal 16 may remain in place to later be drawn backwards, as may be the case for a fill at time-of-use filling process. The barrel adapters and safety syringes described herein are configured such that they may readily be manufactured individually, or in a group, as is the case in a tray-based manufacturing and filling process.

The safety syringes of the present invention are configured to be used in a manner similar to conventional syringes. The method of use includes the steps: depressing the plunger assemble 12 to facilitate delivery of a drug from the barrel 18; upon completion of the drug delivery, triggering the locking mechanism 22 to release the biasing member from its energized state; and, by contact between the biasing member and the needle assembly 42, causing the needle assembly 42 to retract into the barrel 18. As discussed above with regard to the embodiments of the syringes, there are a number of different ways that the locking mechanism 22, release ring, needle hub 24, and other components may be configured to function to enable the engagement and release of the biasing member. For example, in syringe 10, the locking mechanism 22 may include an interface on the barrel tip 32 which engages the locking mechanism 22. Upon activation by the user, the needle hub 24 may be employed to initiate the release of the locking mechanism 22 from its engagement with the barrel tip 32. In another embodiment of the syringe, the locking aspects 32a may be separate components from barrel tip 32, but function in a manner similar to the components of syringe 10.

Regardless of the particular components, the methods of use for the safety syringes of the present invention are relatively similar. By releasing the locking mechanism 22 from its engaged condition, the biasing member 30 is allowed to expand causing the needle assembly 42 to retract in the proximal direction substantially along a longitudinal axis of the barrel 18. In some embodiments of the present invention, the entire needle assembly 42 is caused to retract, while in other embodiments only certain components thereof, including the needle 28, are caused to retract upon release of the locking mechanism 22 and activation of the biasing member 30. Similarly, in some embodiments of the present invention, the locking mechanism is caused to retract with the needle assembly 42 while in other embodiments the locking mechanism remains substantially stationary, but enables the needle assembly 42, or components thereof, to move. Optionally, the method of use may include the step of blocking, with a needle block 34, the needle 28 from axially translating in the distal direction after the needle assembly 42 has retracted into the barrel 18, such as, by way of example only, needle block 54.

FIGS. 8a-8d show a syringe 10 including a barrel adapter 20 according to one embodiment of the present invention, as the syringe 10 progresses through the stages of: needle injection, drug dose delivery, retraction activation, and needle retraction. FIGS. 9a-9d show expanded cross-sectional views of the embodiment shown in FIGS. 8a-8d, showing the relationship of the components as the syringe 10 progresses through the stages of: needle injection, drug dose delivery, retraction activation, and needle retraction.

Figure 8A:
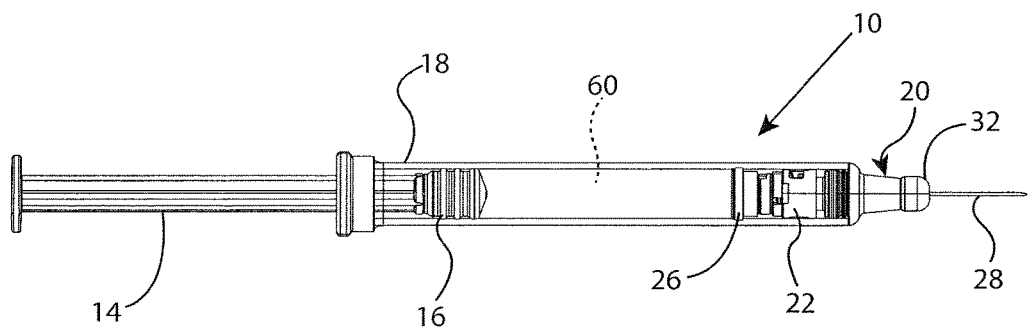
FIGS. 8a-8d show side views of a syringe including a barrel adapter according to an embodiment of the present invention, as the syringe progresses through the stages of needle injection, drug dose delivery, retraction activation, and needle retraction.
Figure 8B:
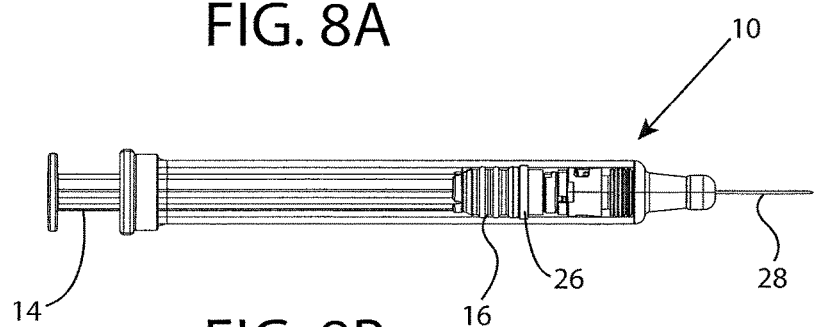
Figure 8C:
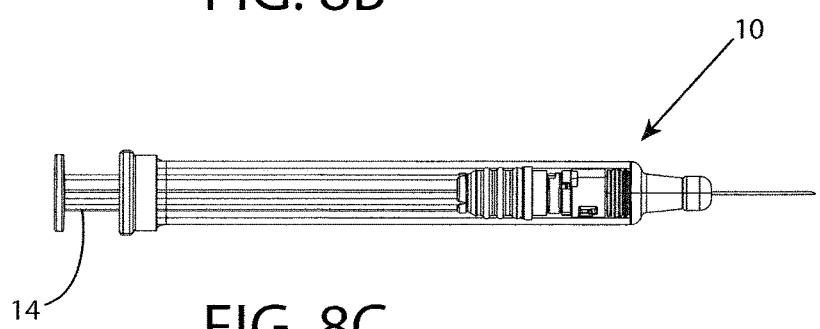
Figure 8D:
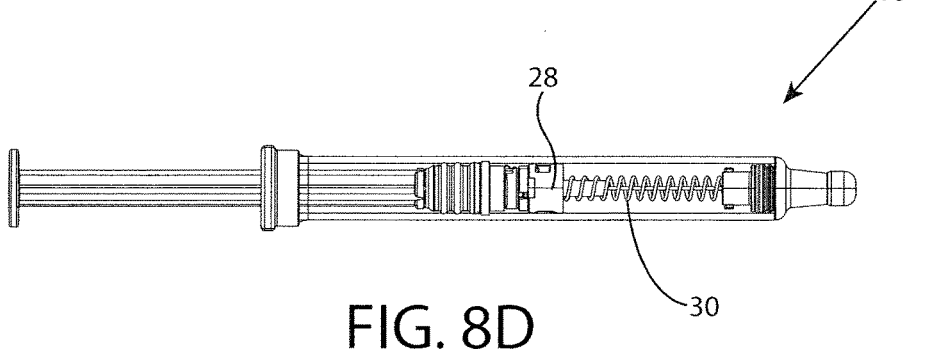
Figure 9A:
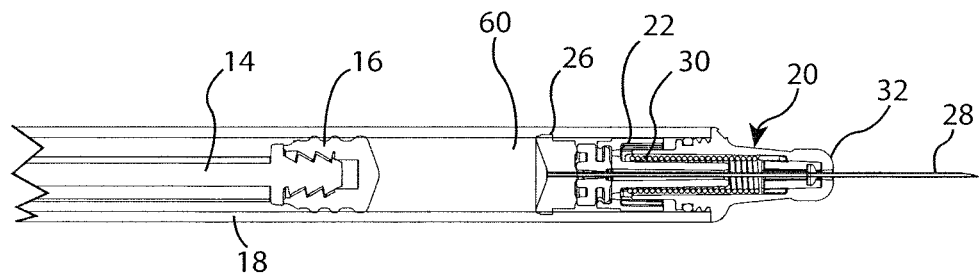
FIGS. 9a-9d show enlarged, fragmentary cross-sectional views of the embodiment shown in FIGS. 8a-8d, similarly as the syringe progresses through the stages of: needle injection, drug dose delivery, retraction activation, and needle retraction.
Figure 9B:
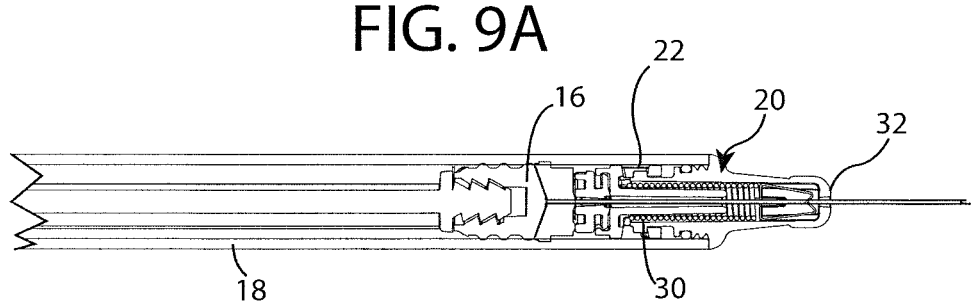
Figure 9C:
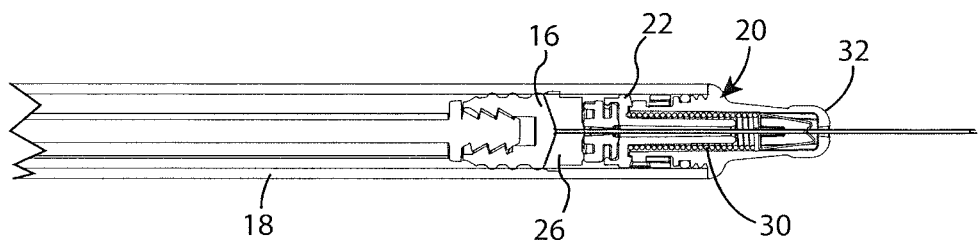
Figure 9D:
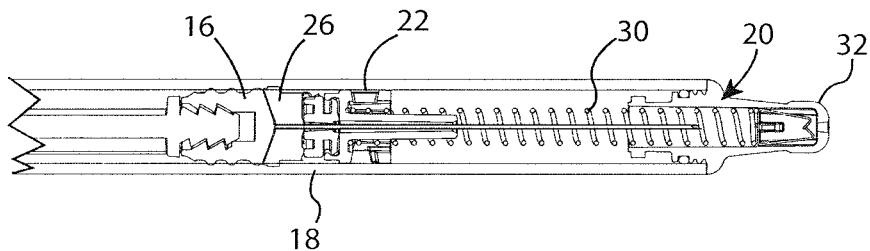

FIG. 8a shows the barrel adapter 20 mounted with the barrel 18. In packaging, the barrel adapter 20 may contain a rigid needle shield (RNS—not shown in FIGS. 8a-8d) which removably engages with barrel tip 32 to protect the user from the needle 28. FIG. 8a shows the syringe 10 with the RNS removed and the needle 28 exposed for injection into a patient. The drug chamber 60 of the barrel 18, between the plunger seal 16 and the needle seal 26, contains a drug treatment for injection. FIG. 8b shows the syringe 10 at the end of drug dose delivery, with the plunger rod 14 depressed axially in the distal direction, the plunger seal 16 in contact with the needle seal 26, and substantially all of the drug treatment injected through the needle 28 into the patient. Upon minimal further depression of the plunger rod 14, the retraction mechanism is activated. As shown in FIG. 8c, the locking mechanism 22 is permitted to rotate axially by, for example, torsional bias of the biasing member 30. Upon axial rotation of the locking mechanism 22, the locking mechanism 22 is permitted to disengage from the locking aspects 32a of the barrel tip 32 as described above. The biasing member 30 is permitted to expand axially in the proximal direction. The proximal end of the biasing member 30 pushes upon the locking mechanism 22 in the proximal direction, which pushes upon the needle hub 24, the needle seal 26, and the needle 28 causing the needle 28 to retract into the barrel 18. FIG. 8d shows the syringe 10 after needle retraction has completed.

The present invention provides component assemblies, such as barrel adapters, which provide needle retraction, syringes which integrate such safety mechanisms, methods of manufacturing such adapters and safety syringes, and their methods of use. As stated above, the barrel adapters and safety syringes may be utilized in a number of different configurations. For example, as stated above, the novel barrel adapters of the present invention are configured to mate with, be mounted in, or otherwise connect to a barrel, however it may be desirable to pre-form any of the components of the barrel adapter to the barrel. Such modifications are contemplated by and encompassed in the embodiments of the present invention. Similarly, the barrel adapter may contain a needle hub and needle seal, which may be separate components or a dual-purpose single component. Other components may similarly be single components, unified components, or multi-purpose components, as described in the embodiments discussed above. Furthermore, there are a number of different configurations which may utilize the novel needle retraction mechanisms described herein, which may generally be contained substantially within the barrel tip and the distal end of the barrel. Accordingly, similar to the examples provided above, the barrel adapters and safety syringes of the present invention may be configured, modified, and utilized to initiate drug delivery and activate needle retraction in any number of configurations while remaining within the breadth and scope of the present invention. Thus, it is intended that the present invention covers the modifications and variations of this invention provided they come within the scope of the appended claims and their equivalents.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A barrel adapter for a safety syringe having a barrel and a plunger assembly adapted to move within the barrel, the adapter comprising:
 a barrel tip adapted to be sealingly engaged with a distal end of the barrel,
 a needle assembly including a needle, a needle hub through which the needle extends, and a needle seal, the needle assembly being disposed at least partially within the barrel tip, the needle adapted to move from an injection position in which the needle extends from a distal end of the barrel tip to a retracted position in which the needle is disposed within at least one of the barrel tip or the barrel, and a needle retraction mechanism, the needle retraction mechanism including a biasing member and an actuable locking arrangement, the actuable locking arrangement including a locking mechanism releasably coupled to the barrel tip, the locking mechanism being disposed to rotate relative to the needle seal, the biasing member being disposed between the locking mechanism and the barrel tip, the biasing member being disposed in an energized position when the locking mechanism is releasably coupled to the barrel tip, and the biasing member disposed to release energy when the actuable locking arrangement is actuated and the locking mechanism and the barrel tip are decoupled, the locking arrangement being actuable by depression of the plunger assembly, the biasing member being disposed to move the needle from the injection position to the retracted position when the biasing member is released from the energized position, wherein the locking mechanism is rotatable relative to the needle seal during at least one of actuation of the actuable locking arrangement and release of energy from the biasing member.

2. The barrel adapter of claim 1 wherein the actuable locking arrangement includes at least one locking aspect disposed to energize the biasing member.

3. The barrel adapter of claim 2 wherein at least one of the barrel tip and the locking mechanism include at least one locking aspect and the other of the barrel tip and the locking mechanism include at least one corresponding receiving element disposed to releasably engage with the locking aspect.

4. The barrel adapter of claim 1 wherein the locking arrangement is actuable by at least one of compression or torsion.

5. The barrel adapter of claim 4 wherein the biasing member includes a torsionally biased compression spring, and the locking arrangement is actuable by torsion.

6. The barrel adapter of claim 1 wherein the needle assembly is disposed at least partially proximally the locking mechanism.

7. The barrel adapter of claim 6 wherein the biasing member includes a torsionally compressed spring disposed to rotate the locking mechanism when releasing energy.

8. An automatically retractable safety syringe comprising
a barrel having a distal end and a proximal end,
a plunger assembly adapted to move within the barrel, and
the barrel adapter of claim 1 sealingly engaged with the distal end of the barrel.

9. The safety syringe adapter of claim 8 wherein the locking arrangement is actuable by at least one of compression or torsion.

10. The barrel adapter of claim 1 further comprising a needle block disposed to block movement of the needle distally through the barrel tip when the needle is in the retracted position.

11. The barrel adapter of claim 1 wherein the needle retraction mechanism is disposed at least partially within the barrel tip.

12. The barrel adapter of claim 1 wherein the locking mechanism engages the needle assembly.

13. The barrel adapter of claim 1 wherein the barrel tip is sized to engage a commercially available syringe.

14. A method of assembling an automatically retractable safety syringe, the method comprising:
assembling a needle retraction subassembly by disposing a biasing member between a barrel tip and a locking mechanism, and releasably coupling the locking mechanism to the barrel tip to hold the biasing member in an energized position,
disposing a plunger assembly to move within a barrel,
disposing a needle assembly between the barrel and the needle retraction subassembly, the needle assembly being disposed for movement within the barrel tip and the barrel between an injection position wherein a needle of the needle assembly extends from the barrel tip and a retracted position wherein the needle is disposed within at least one of the barrel tip or the barrel, the locking mechanism being rotatably disposed relative to a needle seal of the needle assembly and relative to the needle tip when the locking mechanism and the barrel tip are decoupled, and
sealingly engaging the barrel tip with a distal end of the barrel such that the locking mechanism is actuable by depression of the plunger assembly, the biasing member being disposed to rotate the locking mechanism and move the needle from the injection position to the retracted position when the biasing member is released from the energized position.

15. The method of claim 14 further comprising providing a barrel adapter comprising the needle assembly, the needle retraction mechanism, and the barrel tip.

16. The method of claim 14 wherein assembling the needle retraction subassembly includes applying a torsional force to the locking mechanism relative to the barrel tip.

17. The method of claim 14 wherein disposing the needle assembly includes the steps of inserting a needle of the needle assembly through the barrel tip and inserting the needle seal into the distal end of the barrel.

18. The method of claim 14 wherein sealingly engaging includes utilizing an adapter to sealingly engage the barrel tip with the distal end of the barrel.

19. The method of claim 14 wherein disposing a plunger assembly to move within a barrel includes disposing the plunger assembly to move within a commercially available barrel.

20. A barrel adapter for a safety syringe having a barrel and a plunger assembly adapted to move within the barrel, the adapter comprising:
a barrel tip adapted to be sealingly engaged with a distal end of the barrel,
a needle assembly including a needle, a needle hub through which the needle extends, and a needle seal, the needle assembly being disposed at least partially within the barrel tip, the needle adapted to move from an injection position in which the needle extends from a distal end of the barrel tip to a retracted position in which the needle is disposed within at least one of the barrel tip or the barrel, and
a needle retraction mechanism, the needle retraction mechanism including a biasing member and an actuable locking arrangement, the actuable locking arrangement including a locking mechanism releasably coupled to the barrel tip, the locking mechanism being disposed to rotate relative to the needle seal, the locking mechanism being adapted to release and separate from the barrel tip when actuated, the biasing member being disposed between the locking mechanism and the barrel tip, the biasing member being disposed in an energized position when the locking mechanism is releasably coupled to the barrel tip, and the biasing member disposed to release energy when the actuable locking arrangement is actuated and the locking mechanism and the barrel tip are decoupled and separated, the locking arrangement being actuable by depression of the plunger assembly, the biasing member being disposed to rotate the locking mechanism and move the needle from the injection position to the retracted position when the biasing member is released from the energized position.

* * * * *